US012042133B2

(12) United States Patent
Dreyfuss et al.

(10) Patent No.: US 12,042,133 B2
(45) Date of Patent: Jul. 23, 2024

(54) SYSTEM PROVIDING IMPROVED VISIBILITY FOR MINIMALLY INVASIVE SURGERY SYSTEMS

(71) Applicant: ARTHREX, INC., Naples, FL (US)

(72) Inventors: Peter Dreyfuss, Naples, FL (US); Zachary A. Kemp, Naples, FL (US); Tim E. Adamson, Charlotte, NC (US); Michael Gallizzi, Denver, CO (US); Wade K. Jensen, North Sioux City, ND (US); G. Joshua Karnes, Estero, FL (US); Shane J. Noble, Naples, FL (US)

(73) Assignee: Arthrex, Inc., Naples, FL (US)

( * ) Notice: Subject to any disclaimer, the term of this patent is extended or adjusted under 35 U.S.C. 154(b) by 477 days.

(21) Appl. No.: 17/314,990

(22) Filed: May 7, 2021

(65) Prior Publication Data

US 2022/0354359 A1 Nov. 10, 2022

(51) Int. Cl.
*A61B 1/31* (2006.01)
*A61B 1/00* (2006.01)
(Continued)

(52) U.S. Cl.
CPC ........ *A61B 1/3132* (2013.01); *A61B 1/00105* (2013.01); *A61B 1/042* (2013.01);
(Continued)

(58) Field of Classification Search
CPC ............ A61B 17/3423; A61B 17/3439; A61B 2017/3443; A61B 2017/3445; A61B 2017/3447; A61B 2017/3466
See application file for complete search history.

(56) References Cited

U.S. PATENT DOCUMENTS 5,746,720 A * 5/1998 Stouder, Jr. ........ A61B 17/3417
604/23
5,810,712 A 9/1998 Dunn
(Continued)

FOREIGN PATENT DOCUMENTS

EP 2770922 4/2017
WO WO-9219146 A1 * 11/1992 ......... A61B 17/2909
(Continued)

OTHER PUBLICATIONS

"ML-2000 Set", Tedan Surgical Innovations, tedansurgical.com, May 10, 2017 https://web.archive.org/web/20170510210747/https://www.tedansurgical.com/ml-2000-set/.
(Continued)

*Primary Examiner* — Anu Ramana
(74) *Attorney, Agent, or Firm* — Greenberg Traurig, LLP; Michael K. Dixon

(57) ABSTRACT

A modular access medical system configured to enable a surgeon to conduct a medical procedure in fluid contained within a defined space is disclosed. As such, the system increases visibility to an operating surgeon by eliminating smoke and other vapors formed during use of a medical instrument at the surgical site. The modular access medical system may be formed from a distal end of a cannula configured to be placed into contact with tissue such that fluid can be administered within the cannula and retained therein to facilitate a surgical procedure to be conducted via one or more instruments extending through fluid contained within the cannula.

21 Claims, 13 Drawing Sheets

(51) Int. Cl.
*A61B 1/04* (2006.01)
*A61B 1/313* (2006.01)
*A61B 17/34* (2006.01)

(52) U.S. Cl.
CPC ...... *A61B 17/3423* (2013.01); *A61B 17/3439* (2013.01); *A61B 2217/005* (2013.01)

(56) References Cited

U.S. PATENT DOCUMENTS

| | | | |
|---|---|---|---|
| 5,814,026 A * | 9/1998 | Yoon | A61B 17/3462 604/539 |
| 5,913,847 A * | 6/1999 | Yoon | A61B 17/3462 604/523 |
| 5,957,888 A * | 9/1999 | Hinchliffe | A61B 17/3421 606/174 |
| 5,984,937 A * | 11/1999 | Morse | A61B 17/00008 606/45 |
| 6,017,356 A * | 1/2000 | Frederick | A61B 17/3417 606/167 |
| 6,197,002 B1 * | 3/2001 | Peterson | A61B 17/3462 604/164.01 |
| 7,226,451 B2 | 6/2007 | Shluzas et al. | |
| 7,338,441 B2 | 3/2008 | Houser et al. | |
| 7,828,775 B2 | 11/2010 | Okoniewski | |
| 7,854,724 B2 * | 12/2010 | Stearns | A61B 17/3474 604/23 |
| D665,905 S | 8/2012 | Oberlaender | |
| 8,235,999 B2 | 8/2012 | Simonson | |
| 8,298,139 B2 | 10/2012 | Hamada | |
| 8,353,873 B2 | 1/2013 | Sakai | |
| 8,372,131 B2 | 2/2013 | Hestad | |
| D678,523 S | 3/2013 | Shibao | |
| 8,394,015 B2 | 3/2013 | Dibiasio et al. | |
| 8,460,186 B2 | 6/2013 | Ortiz | |
| 8,568,308 B2 | 10/2013 | Reznik | |
| 8,636,657 B2 | 1/2014 | Hamada | |
| 8,641,608 B2 | 2/2014 | Voegele et al. | |
| 8,727,974 B2 | 5/2014 | Kasvikis | |
| 8,771,181 B2 | 7/2014 | Garcia-Bengochea | |
| 8,876,709 B2 | 11/2014 | Vayser | |
| 8,888,689 B2 | 11/2014 | Poll et al. | |
| 8,906,094 B2 | 12/2014 | Roche et al. | |
| 8,915,845 B2 | 12/2014 | Pell et al. | |
| 9,095,299 B2 | 8/2015 | Ray | |
| 9,107,650 B2 | 8/2015 | Bjork | |
| 9,125,587 B2 | 9/2015 | Hawkins et al. | |
| 9,220,402 B2 | 12/2015 | Roth et al. | |
| 9,402,537 B2 | 8/2016 | Nadershahi et al. | |
| 9,532,801 B2 | 1/2017 | Davis | |
| 9,610,095 B2 | 4/2017 | To et al. | |
| 9,833,282 B2 | 12/2017 | Jun | |
| 9,861,428 B2 | 1/2018 | Trees et al. | |
| 9,867,605 B2 | 1/2018 | Adams | |
| 9,918,709 B2 | 3/2018 | Sandhu | |
| 9,962,520 B2 | 5/2018 | Mastri et al. | |
| 10,045,768 B2 | 8/2018 | Garcia-Bengochea | |
| 10,245,070 B2 | 4/2019 | Flom | |
| 10,327,751 B2 | 6/2019 | Coe et al. | |
| 10,390,694 B2 | 8/2019 | Farin | |
| 2005/0124988 A1 | 6/2005 | Terrill-Grisoni | |
| 2006/0200185 A1 * | 9/2006 | Marchek | A61B 17/3421 606/191 |
| 2007/0088277 A1 | 4/2007 | McGinley et al. | |
| 2007/0203402 A1 * | 8/2007 | Godara | A61B 18/1477 600/300 |
| 2007/0208229 A1 | 9/2007 | Prusmack | |
| 2008/0228213 A1 | 9/2008 | Blakeney | |
| 2009/0287061 A1 | 11/2009 | Feigenbaum | |
| 2010/0240959 A1 | 9/2010 | Donahue | |
| 2011/0144437 A1 | 6/2011 | Ortiz et al. | |
| 2011/0144444 A1 * | 6/2011 | Sakai, Jr. | A61B 1/32 600/206 |
| 2011/0201883 A1 | 8/2011 | Cooper et al. | |
| 2012/0010670 A1 | 1/2012 | Pisarnwongs et al. | |
| 2012/0130186 A1 | 5/2012 | Stopek et al. | |
| 2014/0018732 A1 | 1/2014 | Bagaoisan et al. | |
| 2014/0275793 A1 | 9/2014 | Song | |
| 2017/0215857 A1 | 8/2017 | D'urso | |
| 2017/0215860 A1 | 8/2017 | Trimarche | |
| 2018/0098788 A1 | 4/2018 | White | |
| 2018/0098789 A1 | 4/2018 | White | |
| 2018/0317899 A1 | 11/2018 | Zada | |
| 2019/0110786 A1 | 4/2019 | Ip et al. | |
| 2019/0183476 A1 | 6/2019 | Garcia-Bengochea | |
| 2019/0231450 A1 | 8/2019 | Waterbury | |
| 2019/0262591 A1 | 8/2019 | Jayol | |
| 2020/0001025 A1 | 1/2020 | Geisz et al. | |
| 2020/0405416 A1 | 12/2020 | Shelton, IV et al. | |
| 2021/0128196 A1 | 5/2021 | Carroll et al. | |

FOREIGN PATENT DOCUMENTS

| | | |
|---|---|---|
| WO | 2015042403 | 3/2015 |
| WO | 2018156638 | 8/2018 |

OTHER PUBLICATIONS

"Spotlight MIS Access System", DePuy Synthes, synthes.vo.llnwd.net, Nov. 18, 2017 https://web.archive.org/web/20171118131745/http://synthes.vo.llnwd.net/o16/LLNWMB8/INT%20Mobile/Synthes%20International/Product%20Support%20Material/legacy_Synthes_PDF/9086-58-000.pdf.

"ProView MAP System", Orthofix, orthofix.com, Aug. 22, 2019 http://webcache.googleusercontent.com/search?q=cache:h8Wb0Q3C0ScJ:web.orthofix.com/Products/Pages/ProView-MAP-System.aspx%3Fcatid%3D18+&cd=1&hl=en&ct=cInk&gl=us.

"Viewline Tube Retraction System—Reference Guide," Zimmer Spine, 2013 https://www.zimmerbiomet.com/content/dam/zimmer-biomet/medical-professionals/000-surgical-techniques/spine/viewline-tube-retraction-system-reference-guide.pdf.

"Tube Retractor," Seaspine, Accessed 2019 https://www.seaspine.com/products/tube-retractor/.

MedFix Vision 18, 22, and 26MM complete MIS Tubular Retractor Set, MedFix International, Accessed 2019 https://medfix.com/product/medfix-vision-18-22-and-26mm-complete-trs-tubular-retractor-set/.

United States Patent and Trademark Office; PCT International Search Report, issued in connection to application No. PCT/US22/27582; 2 pages; Jul. 20, 2022; US.

United States Patent and Trademark Office; PCT Written Opinion of the International Searching Authority, issued in connection to application No. PCT/US22/27582; 13 pages; Jul. 20, 2022; US.

* cited by examiner

SYSTEM PROVIDING IMPROVED VISIBILITY FOR MINIMALLY INVASIVE SURGERY SYSTEMS

BACKGROUND

The disclosure relates generally to minimally invasive surgery systems. More particularly, this disclosure related to handheld, minimally invasive surgery systems for spinal procedures.

Access ports have been used effectively in many different surgical procedures to provide surgeons with unobstructed access to surgical sites within human patients. The ports have been provided in different sizes and configurations depending on the surgical procedure. Access ports have been used in minimally invasive surgery systems (MIS) providing surgeons access to surgical sites, such as, but not limited to, patients' spines. Surgical procedures with handheld rotary medical devices with shavers or burrs, ablation system and the like create smoke at the surgical site which great impedes visibility and creates a problem for surgeons. The smoke increases the length of time of a surgical procedure, thereby reducing the efficiency and increasing costs.

SUMMARY

A modular access medical system configured to enable a surgeon to conduct a medical procedure in fluid contained within a defined space is disclosed. As such, the system increases visibility to an operating surgeon by eliminating smoke and other vapors formed during use of a medical instrument at the surgical site. The modular access medical system may be formed from a distal end of a cannula configured to be placed into contact with tissue such that fluid can be administered within the cannula and retained therein to facilitate a surgical procedure to be conducted via one or more instruments extending through fluid contained within the cannula.

In at least one embodiment, the modular access medical system may be formed from a housing having an working channel with a proximal opening and a distal opening. The system may include a cannula extending distally from the housing and forming a channel extending therethrough for receiving at least one instrument, whereby the channel in the cannula is aligned with the working channel of the housing. The cannula may be formed from at least one detachable segment. A distal end of the detachable segment may be configured to be placed into contact with tissue such that fluid can be administered within the cannula and retained therein to facilitate a surgical procedure to be conducted via the instrument extending through fluid contained within the cannula. The at least one detachable segment forming the cannula may be a plurality of detachable segments coupled together and extending distally from the housing. The one or more of the detachable segments may have different lengths than other detachable segments. In at least one embodiment, each of the plurality of detachable segments has a different length than each of the other detachable segments.

The modular access medical system may also include an aspiration port coupled to the housing. An aspiration channel may extend from a proximal opening in the aspiration port, through the housing, and terminate at the working channel of the housing, thereby enabling the modular access medical system to maintain the cannula formed by the detachable segment full of fluid during use.

The modular access medical system may also include one or more dams positioned in the housing to retain the fluids in the working channel of the housing. The dam may seal the working channel of the housing to prevent fluids from passing from the channel in the detachable segments out of the proximal opening of the working channel of the housing. The dam may include one or more instrument receiving slits configured to receive an instrument extending therethrough while being configured to be biased to a resting position in which the slit remains closed. The modular access medical system may also include a plurality of dams, which may be, but are not limited to being, stacked together.

The modular access medical system may also include an instrument securement system positioned adjacent the housing for retaining an instrument in position within the working channel in the housing and the channel in the detachable segment. The instrument securement system may include a plurality of instrument receivers. The modular access medical system may also include a housing positioning arm extending generally radially outward from an outer surface of the housing.

A method of conducting a surgical procedure on a patient via a modular access medical system is also disclosed. The method may include obtaining access to a target surgical site within a patient and positioning at least a portion of the modular access medical system within the patient. The modular access medical system may include one or more of the components disclosed herein and other components not disclosed herein or yet to be invented. The method may also include placing the distal end of the cannula in contact with tissue of a patient to seal the distal end, filling the cannula with fluid, inserting the instrument into the fluid, and conducting one or more surgical procedures on the patient with one or more instruments in the fluid. The method may also include aspirating fluid to remove excess fluid so that fluid does not flow out of the proximal opening in the housing. The step of aspirating fluid may be continuous to maintain a desired fluid level. The cannula may also be topped off with fluid throughout a procedure to account for fluid leaking from the distal end of the cannula formed by the detachable segment.

An advantage of the modular access medical system is that the system enables a surgeon to conduct a medical procedure on a target site of a patient, such as, but not limited to, a portion of a human spine in fluid, thereby vastly improving visibility by eliminating smoke generated by the medical instrument working on tissue such as bone, cartilage and the like.

Another advantage of the modular access medical system is that the system enables the length of the cannula to be adjusted to fit a particular procedure and patient.

Yet another advantage of the modular access medical system is that the aspiration port is positioned at a proximal end (upper end) of the system so that the aspiration system can maintain fluid at a desired level without being overly sensitive to an inflow rate of fluid into the cannula.

Another advantage of the modular access medical system is that one or more medical instruments may be held in position in the cannula and may extend through the dam, which prevents unintended spillage of the fluid contained within the cannula.

These and other embodiments are described in more detail below.

DETAILED DESCRIPTION

Figure 1:
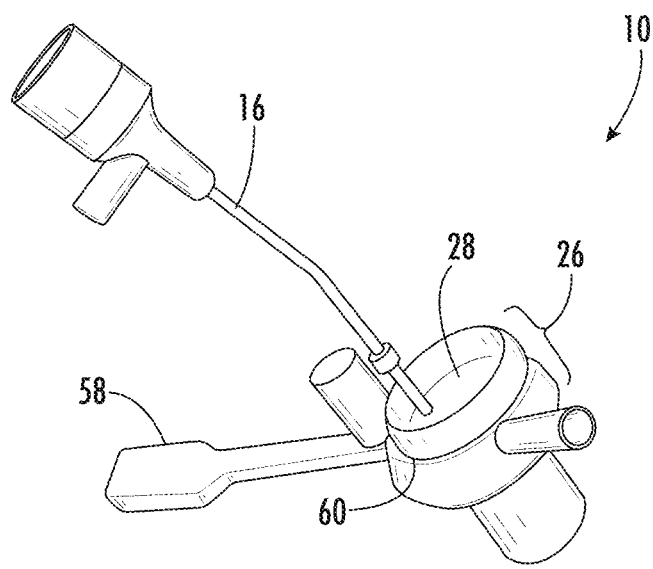
FIG. 1 is a perspective view of a portion of the modular access medical system.
Figure 2:
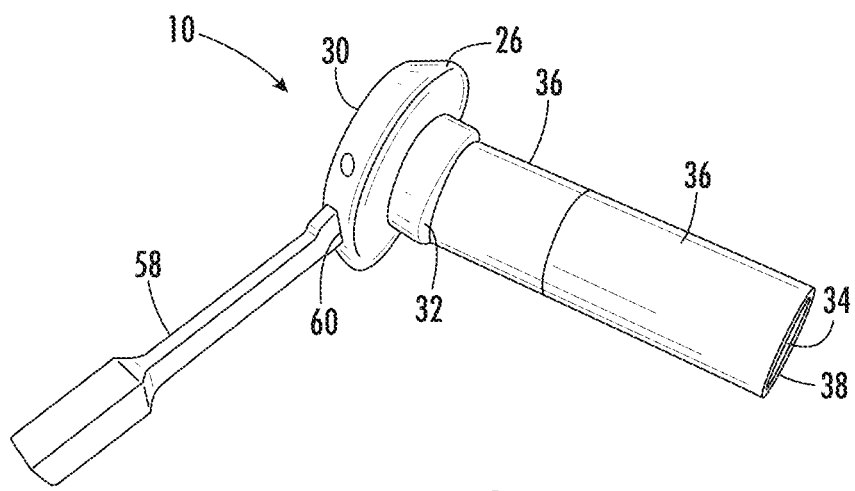
FIG. 2 is a side view of the modular access medical system.
Figure 3:
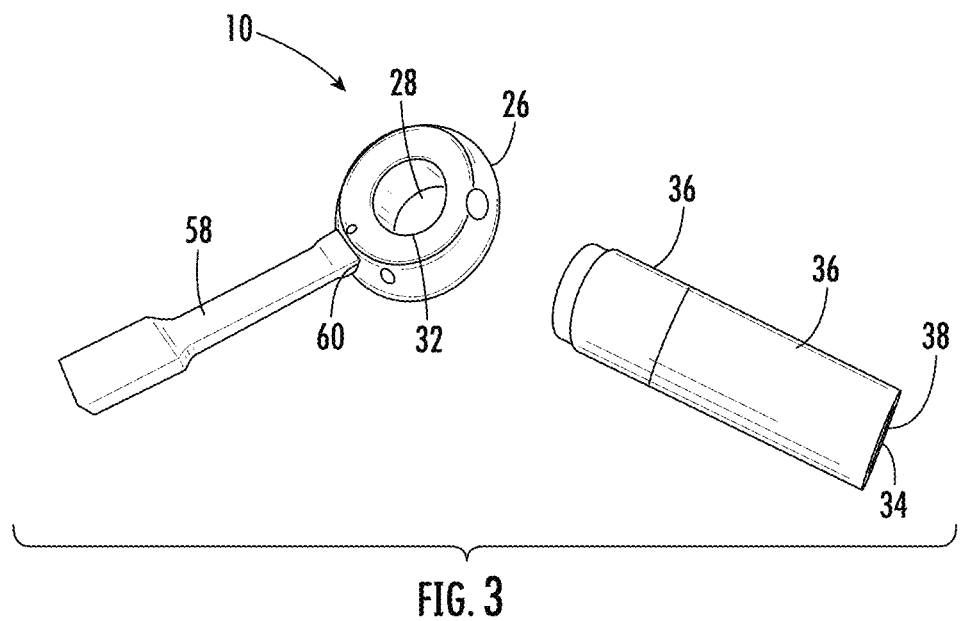
FIG. 3 is a partial exploded view of the modular access medical system.
Figure 4:
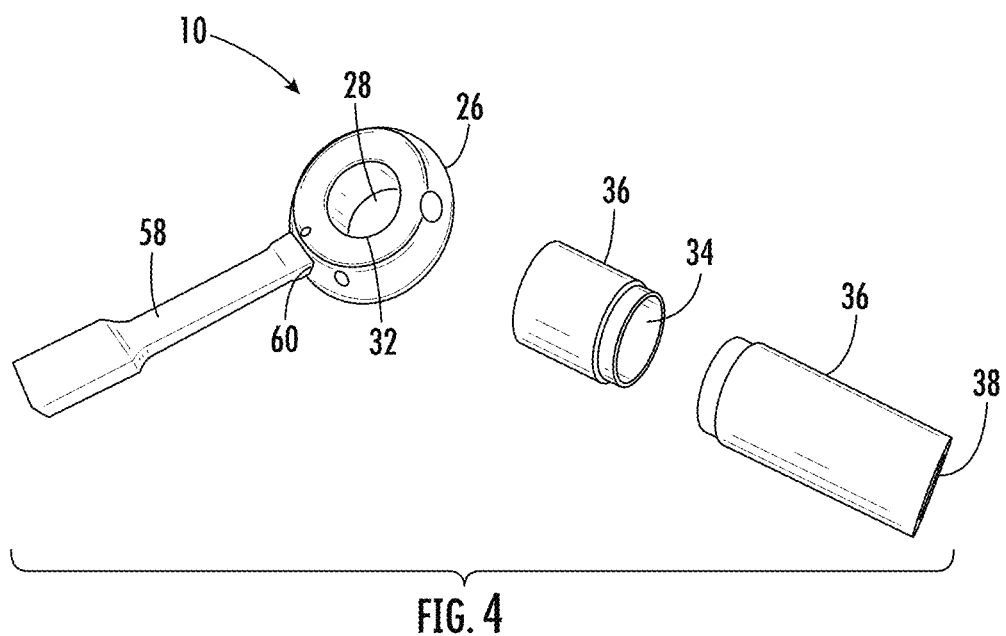
FIG. 4 is an exploded view of the modular access medical system.

As shown in FIGS. 1-19, a modular access medical system 10 configured to enable a surgeon to conduct a medical procedure in fluid 12 contained within a defined space 14 is disclosed. As such, the system 10 increases visibility to an operating surgeon by eliminating smoke and other vapors formed during use of a medical instrument 16 at the surgical site 18. The modular access medical system 10 may be formed from a distal end 38 of a cannula 22 configured to be placed into contact with tissue 24 such that fluid 12 can be administered within the cannula 22 and retained therein to facilitate a surgical procedure to be conducted via one or more instruments 16 extending through fluid 12 contained within the cannula 22. During use, the distal end 38 of a cannula 22 is pushed into contact with a patient's tissue surrounding a surgical site forming a tight fit that prevents fluid contained within the cannula 22 from leaking out.

In at least one embodiment, as shown in FIGS. 1-8, the modular access medical system 10 may be formed form a housing 26 having an working channel 28 with a proximal opening 30 and a distal opening 32. The housing 26 may be cylindrical or have another appropriate configuration. The housing 26 may have a diameter and depth in a direction from the proximal opening 30 of the working channel 28 to the distal opening 32 of the working channel 28 sufficient to support the detachable segments 36. The housing 26 may be formed from an appropriate material, such as, but not limited to, metal, such as, but not limited to, aluminum, brass and steel and plastics, such as, but not limited to, a thermoplastic polymer—acrylonitrile butadiene styrene (ABS), a colorless organic thermoplastic polymer—polyether ether ketone (PEEK) and polycarbonate.

The modular access medical system 10 may also include a cannula 22 extending distally from the housing 26 and forming a channel 34 extending therethrough for receiving one or more instruments 16. The channel 34 in the cannula 22 may be aligned with the working channel 28 of the housing 26. The cannula 34 may be formed from one or more detachable segments 36. A distal end 38 of the detachable segment 36 may be configured to be placed into contact with tissue, such as, but not limited to being, in a human, such that fluid can be administered within the cannula 22 and retained therein to facilitate a surgical procedure to be conducted via the instrument 16 extending through fluid contained within the cannula 22.

In at least one embodiment, the modular access medical system 10 may have a plurality of detachable segments 36 coupled together and extending distally from the housing 26. One or more of the detachable segments 36 may have a different length than other detachable segments 36. In at least one embodiment, of the plurality of detachable segments 36 has a different length than each of the other detachable segments 36. The detachable segments 36 may be available in lengths, such as, but not limited to, 10 millimeters, 20 millimeters and 40 millimeters. One or more of the detachable segments 36 may be cylindrical or have another appropriate configuration. The detachable segments 36 may be formed from an appropriate material, such as, but not limited to, metal, such as, but not limited to, aluminum, brass and steel and plastics, such as, but not limited to, a thermoplastic polymer—acrylonitrile butadiene styrene (ABS), a colorless organic thermoplastic polymer—polyether ether ketone (PEEK) and polycarbonate. The detachable segment 36 may be coupled to the housing 26 and to each other via a releasable connection. The releasable connection, may be, but is not limited to being, threads, snaps, interference fit, and a variety of other methods.

Figure 5:
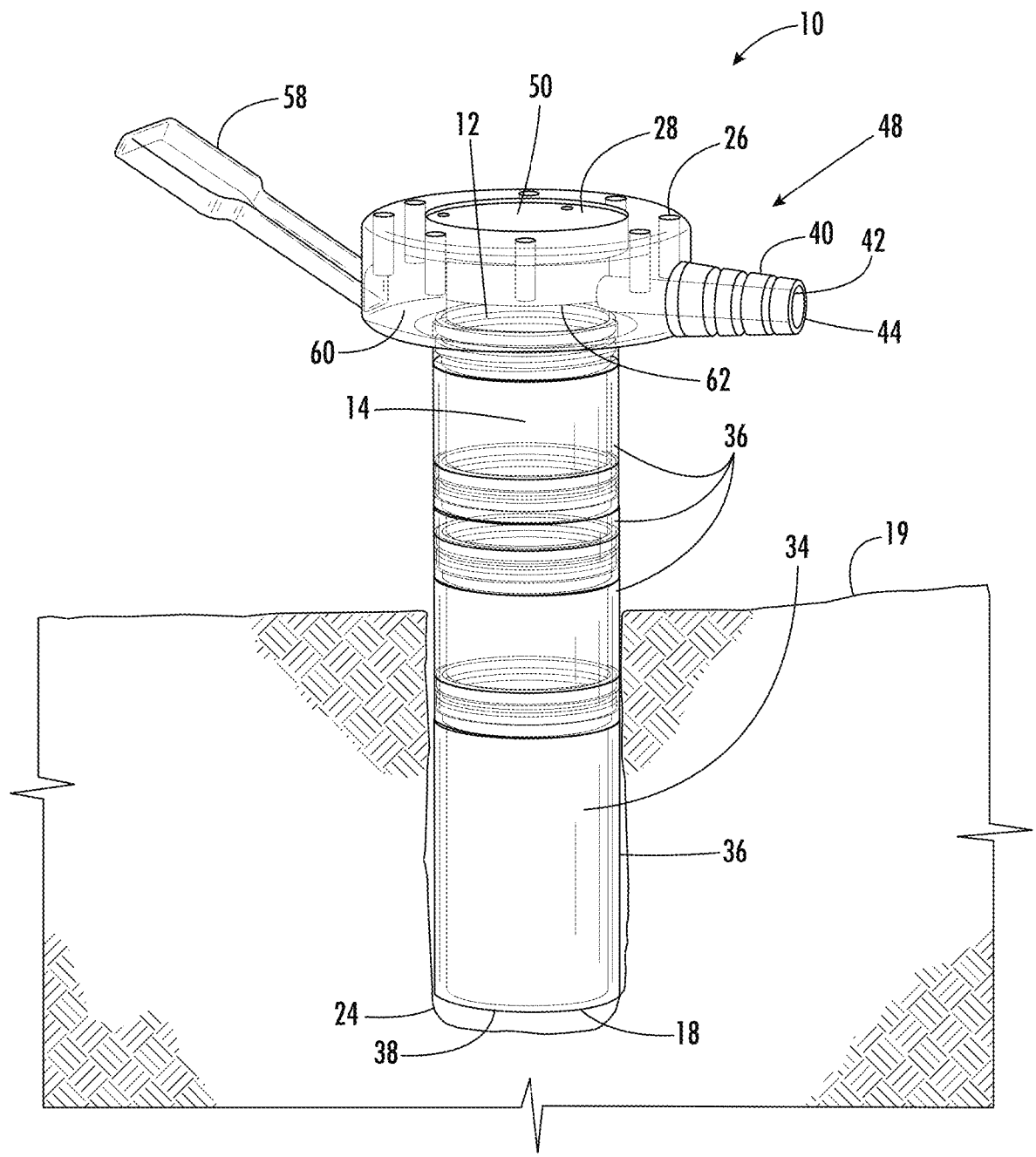
FIG. 5 is a perspective view of the modular access medical system.
Figure 6:
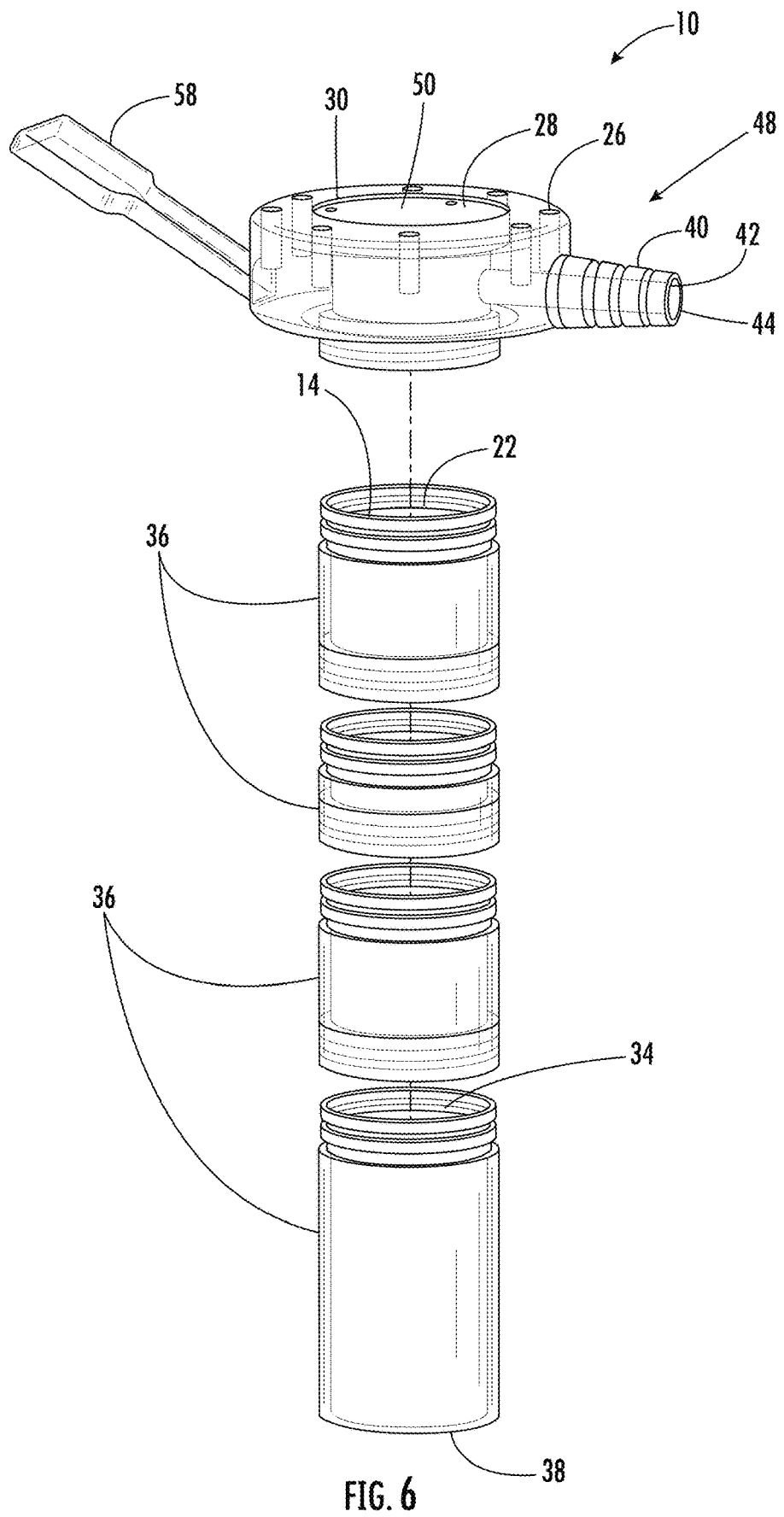
FIG. 6 is an exploded view of the modular access medical system.
Figure 7:
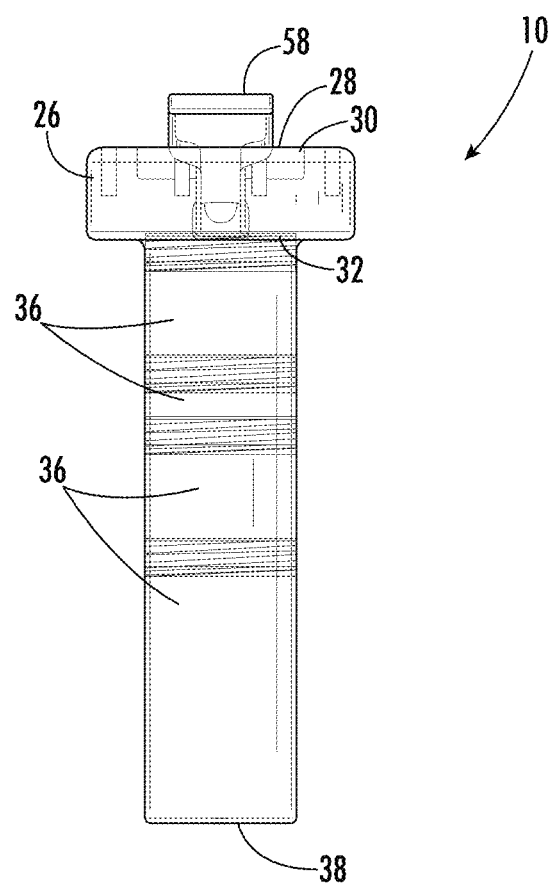
FIG. 7 is a side view of the modular access medical system.
Figure 8:
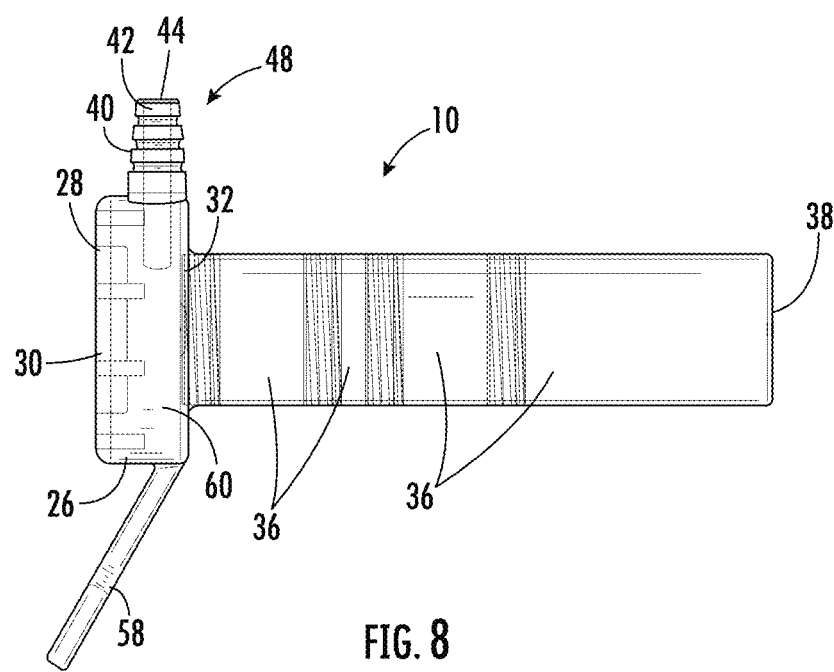
FIG. 8 is an alternative side view of the modular access medical system showing the aspiration port and the housing positioning arm extending generally, radially outward.

The modular access medical system 10, as shown in FIG. 5, may include an aspiration port 40 coupled to the housing 26. The aspiration port 40 may include an aspiration channel 42 extending from a proximal opening 44 in the aspiration port 40, through the housing 26, and terminates at the working channel 28 of the housing 26, thereby enabling the modular access medical system 10 to maintain the cannula 22 formed by the detachable segment 36 full of fluid during use. A suction line may be releasably coupled to the aspiration port 40 via an appropriate connection already existing or yet to be conceived. Positioning the aspiration port 40 at the housing 26, which is typically oriented above the distal end 38 of the detachable segment 36, the aspiration system 48 is self-regulating. As such, a user can't over aspirate fluid from the cannula 22 in the detachable segment 36 because the aspiration port 40 only functions to remove fluids once the fluids reach the level of the aspiration port 40. Such fluid level at the aspiration port 40 only occurs once the entire detachable segment 36 has been filled. In contrast, if an aspiration port 40 were to be placed at the distal end 38 of the detachable segments 36, which also is the bottom of the cannula 22, inflow of fluid into the cannula 22 and outflow of fluid out of the cannula 22 would need to be matched to keep the fluid from either overflowing the cannula 22 and working channel 28 of the housing 26 or over aspirating fluid from the cannula 22 and working channel 28.

Figure 14:
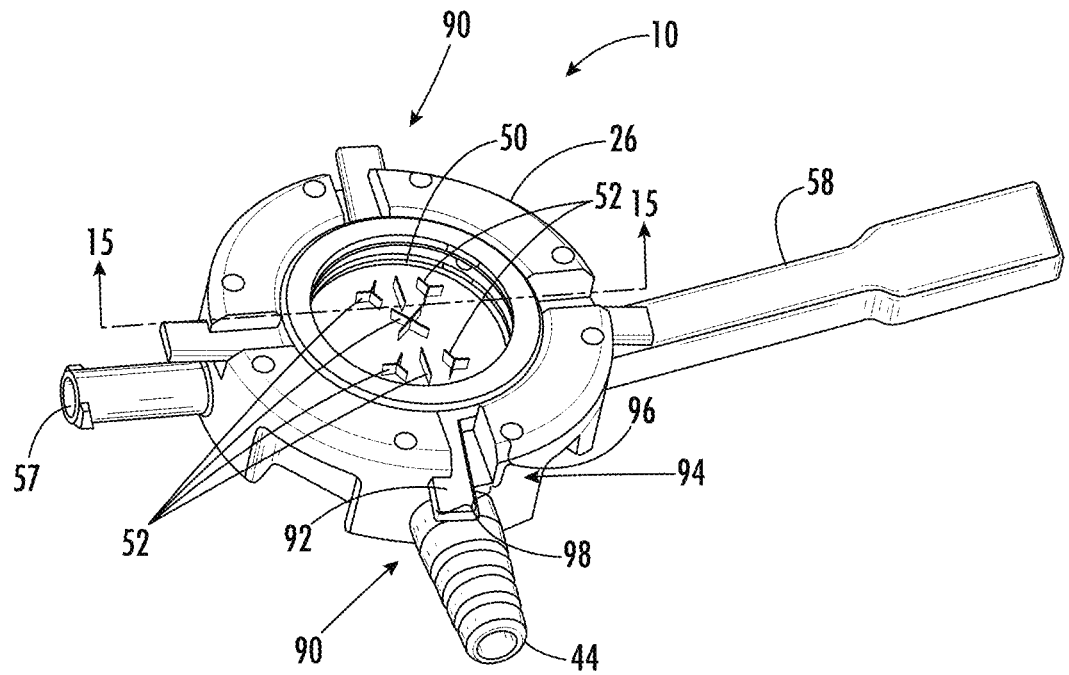
FIG. 14 is a perspective view of a dam with a dam retention system, whereby the dam is positioned within the housing.
Figure 15:
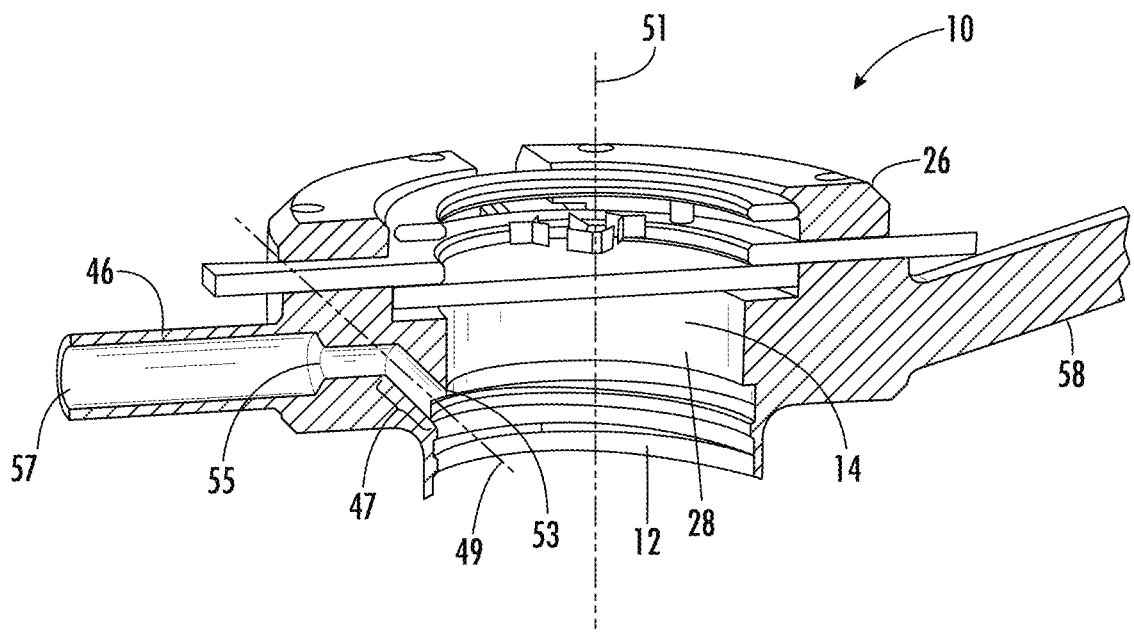
FIG. 15 is cross-sectional perspective view of the housing and dam taken at section line 15-15 in FIG. 14.
Figure 16:
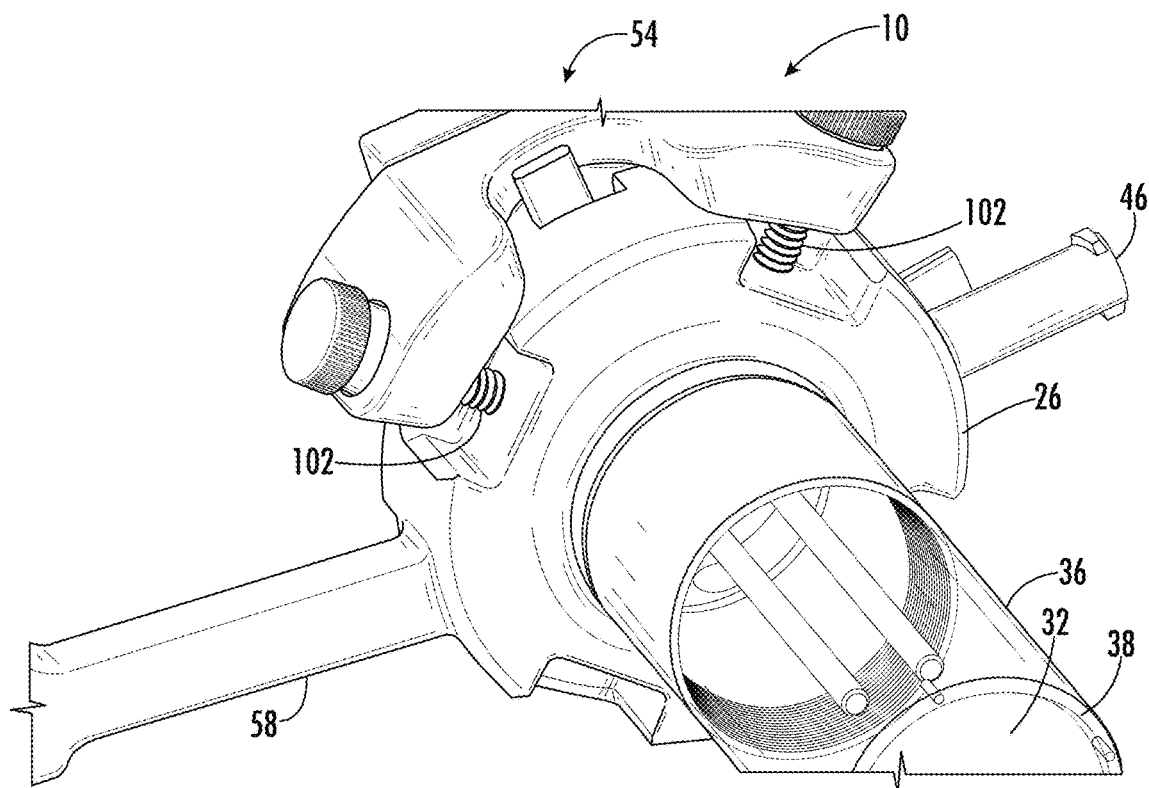
FIG. 16 is a perspective view of the housing with an instrument securement system with multiple releasable connectors secured in receivers in an outer surface of the housing to securely attach an instrument to the housing.
Figure 17:
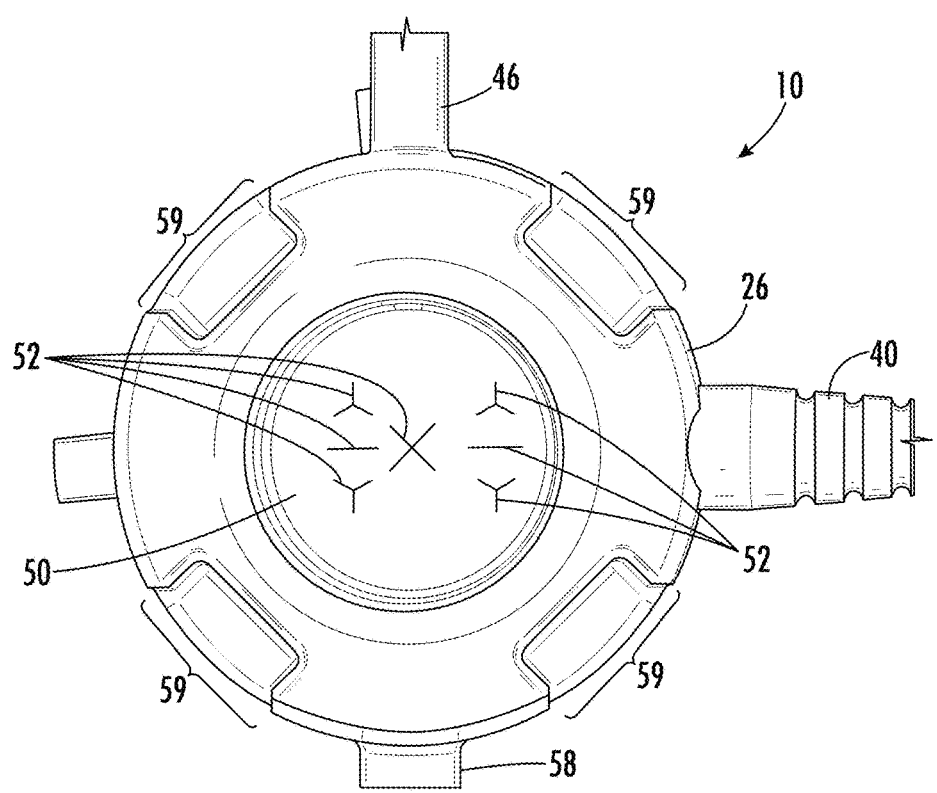
FIG. 17 is a top view of the housing with aspects of the instrument securement system and a dam with a camera positioning system.
Figure 18:
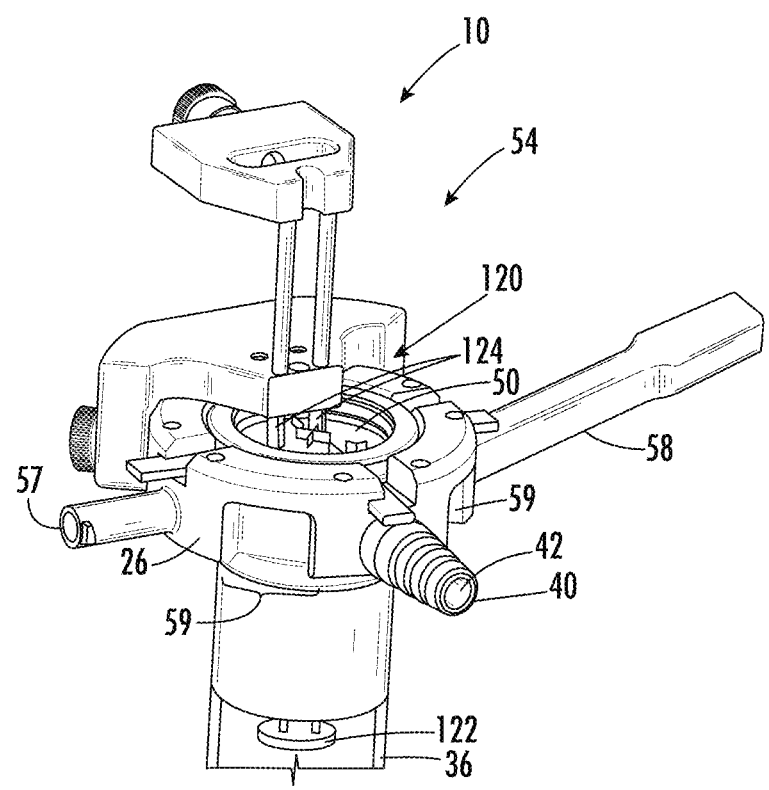
FIG. 18 is a perspective view of a instrument, which is a scope holder, attached to the housing via the instrument securement system and a scope supported by the instrument securement system within the housing and detachable segments.

The modular access medical system 10, as shown in FIGS. 14, 15 and 18, may include an inflow port 46 coupled to the housing 26. The inflow port 46 may be configured to receive fluids and to pass those fluids to the working channel 28 and into the channel 34 defined by the one or more detachable segments 36. The inflow port 46 may include an enhanced fluid exchange section 47 which includes a distally directed vector such that a longitudinal axis 49 of the enhanced fluid exchange section 47 may be nonparallel and nonorthogonal to a longitudinal axis 51 of the housing 26. An outlet 53 of the enhanced fluid exchange section 47 may be closer to the distal end 38 of the detachable segment 36 than an inlet 55 of the enhanced fluid exchange section 47. The inflow port 46 may have any appropriate cross-sectional shape, length and configuration. A proximal end 57 of the inflow port 46 may be configured to receive a releasable connector, such as, but not limited to, a slip tip, such as a LUER LOCK.

Figure 9:
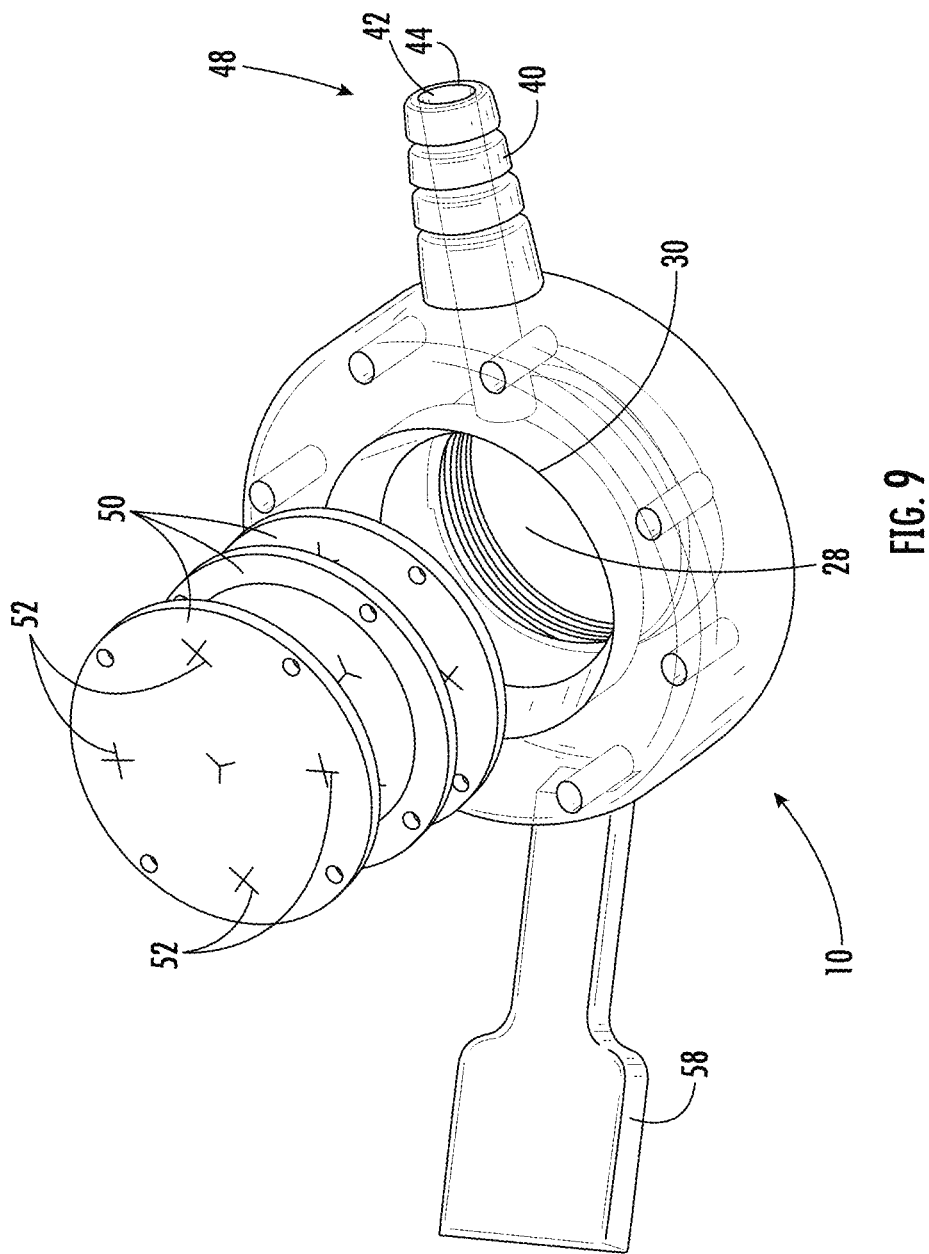
FIG. 9 is an exploded perspective view of the housing of the modular access medical system together with a plurality of dams.
Figure 10:
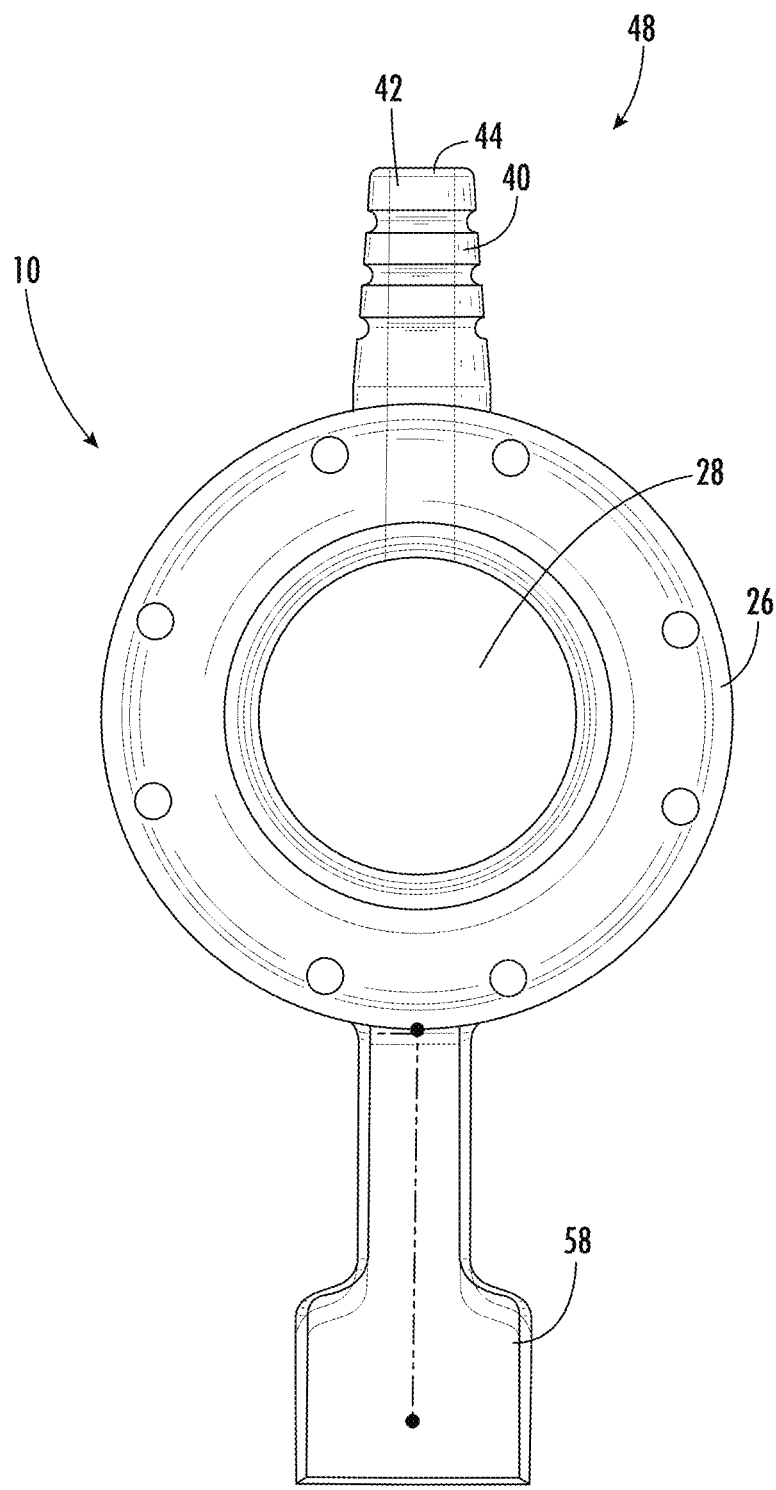
FIG. 10 is a top view of the housing of the modular access medical system.

The modular access medical system 10 may include one or more dams 50, as shown in FIGS. 5 and 9, positioned in the housing 26 to retain the fluids in the working channel 28 of the housing 26. The dam 50 may seal the working channel 28 of the housing 26 to prevent fluids from passing from the channel 28 in the detachable segments 36 out of the proximal opening 30 of the working channel 28 of the housing 26. The dam 50 may include one or more instrument receiving slits 52 configured to receive an instrument 16 extending therethrough while being configured to be biased to a resting position in which the instrument receiving slit 52 remains closed. In at least one embodiment, the modular access medical system 10 may include a plurality of dams 50. In at least one embodiment, the dams 50 may be positioned in the working channel 28 of the housing 26. The dams 50 may be stacked together in the working channel 28 of the housing 26. The dams 50 may be positioned in contact with each other or may be separated from each other. In at least one embodiment, the modular access medical system 10 may be formed from three dams 50 stacked together. The dam 50 provides better fluid retention when the cannula 34 is not exactly vertically oriented but instead is positioned at another angle to prevent fluids from being dumped out of the cannula 34.

The modular access medical system 10 may include one or more dam retention systems 90, as shown in FIGS. 14, 15 and 18, configured to removably attach one or more dams 50 to the housing 26. In at least one embodiment, the dam retention system 90 may include at least one arm 92 extending radially outward from the dam 50 and one or more slots 94 configured to releasably receive the arm 92. The slot 94 may be, but not require to be, shaped as a J-slot formed from a receiver section 96 and a retaining section 98 extending circumferentially from the receiver section 96 for retaining the arm 92 extending radially from the dam 50. The dam 50 and corresponding arm 92 extending from the dam 50 may be attached by positioning the dam 50 to reside within the working channel 28 of the housing 26 and the arm 92 to be received within the slot 94. The dam 50 and arm 92 may be pushed in a distal direction aligned with the longitudinal axis 51 of the housing 26 such that the arm 92 is moved into the receiver section 96. The dam 50 and arm 92 may be rotated to move the arm 92 into the retaining section 98 to retain the arm 92 and the dam 50. In at least one embodiment, the dam retention system 90 may include a plurality of arms 92 extending radially outward from the one or more dams 50. In at least one embodiment, the dam retention system 90 may have, but is not limited to having, four arms 92 extending radially outward from the dam 50.

Figure 11:
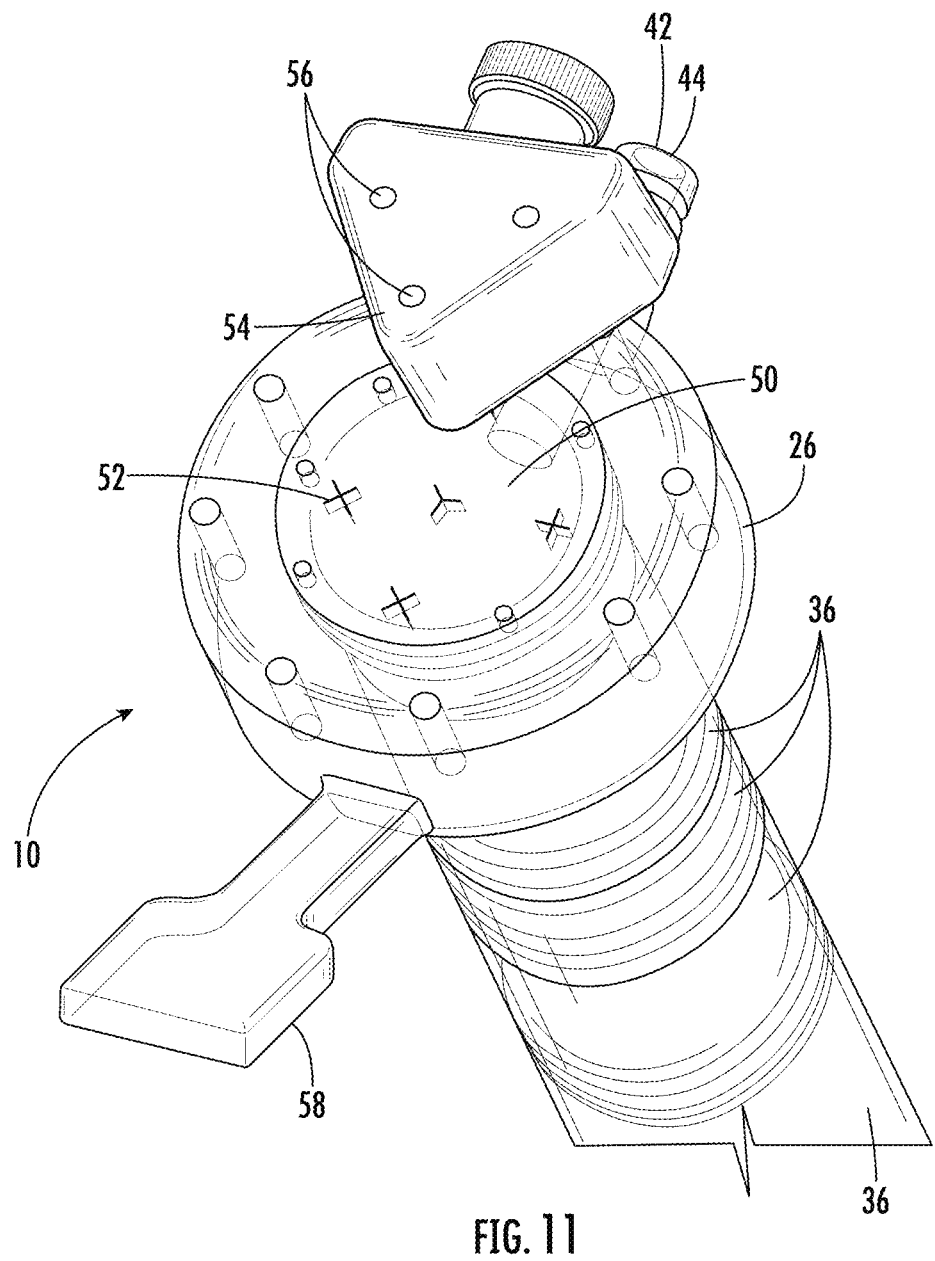
FIG. 11 is a partial perspective view of the housing and detachable segments with an instrument securement system.
Figure 12:
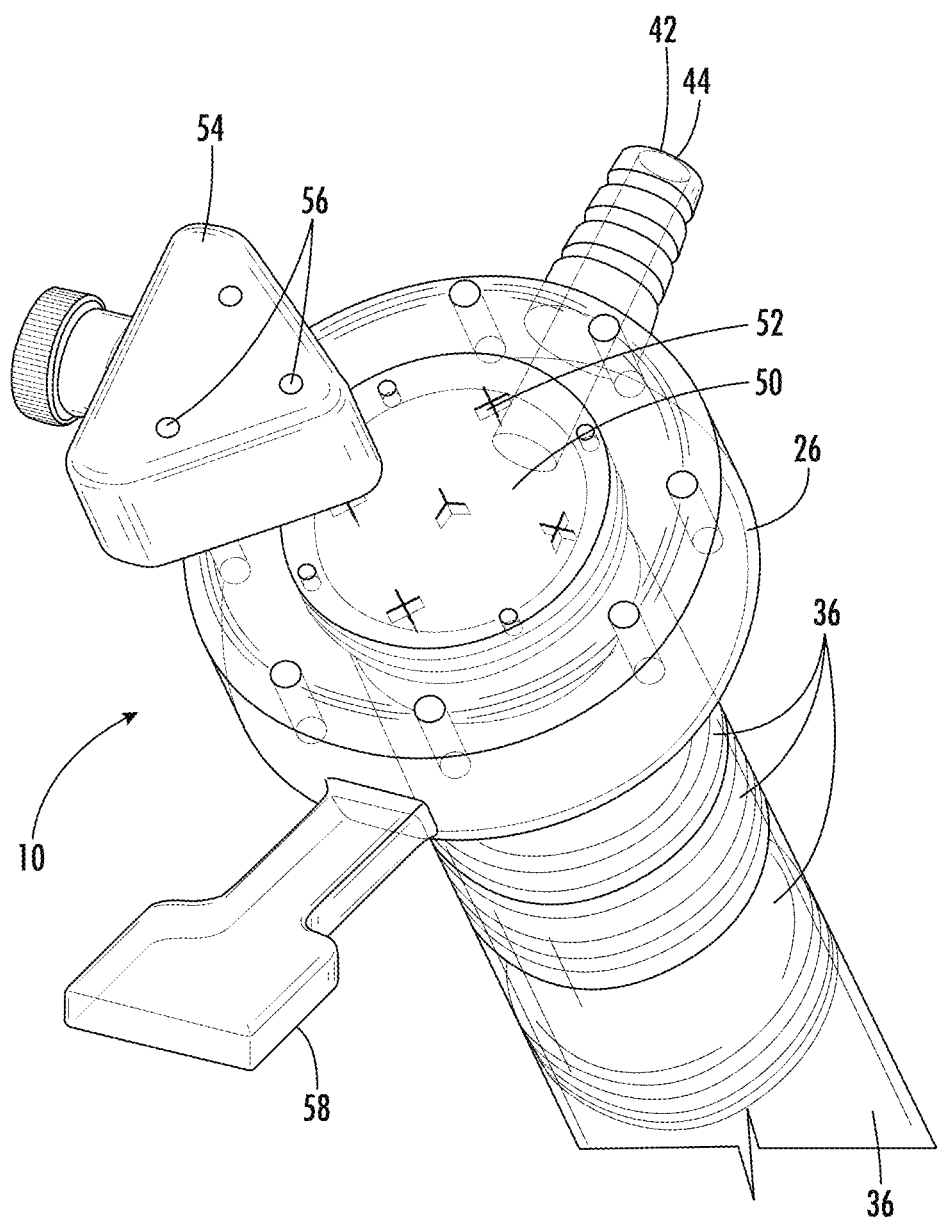
FIG. 12 is another partial perspective view of the housing and detachable segments with an instrument securement system in position rotated 90 degrees from the position shown in FIG. 11.

The modular access medical system 10 may include an instrument securement system 54, as shown in FIGS. 11 and 12, positioned adjacent the housing 26 for retaining an instrument 16 in position within the working channel 28 in the housing 26 and the channel 34 in the detachable segment 36. The instrument securement system 54 may include one or more instrument receivers 56. In at least one embodiment, the instrument securement system 54 may include a plurality of instrument receivers 56. The instrument receiver 56 may be sized to retain a desired instrument 16. The instrument securement system 54 may be generally triangular shaped or have another exterior shape.

In at least one embodiment, as shown in FIGS. 14 and 16-18, the instrument securement system 54 may include one or more receivers 59 positioned in an outer surface 60 of the housing 26. The receiver 59 may be formed from a plurality of receivers 102 offset circumferentially from each other in the outer surface 60 of the housing 26. The configuration of the offset receivers 59 enables an instrument 16 to be secured to the housing 26 in a plurality of different circumferential orientations based on a surgeon's preference, patient position and other factors. The instrument 16 may be, but is not limited to being, a scope holder. In at least one embodiment, the receiver 59 may be a cutout, such as, but not limited to a square cutout, in the outer surface 60 of the housing 26. The instrument securement system 54 may include a plurality of releasable connectors 102, such as, but not limited to, set screws, extending from an instrument 16, such as, but not limited to, a scope holder, and may be received within one or more of the plurality of receivers 59. In at least one embodiment, two releasable connectors 26 may each be received within a different receiver 59, whereby the instrument securement system 54 is prevented from rotating relative to the housing 26.

The modular access medical system 10 may include a housing positioning arm 58 extending generally radially outward from an outer surface 60 of the housing 26, as shown in FIG. 5. The housing positioned arm 58 enables the modular access medical system 10 to be secured in a desired position via an external support system (not shown), which may be any appropriate support system capable of limiting movement of the modular access medical system 10 relative to a patient.

Figure 19:
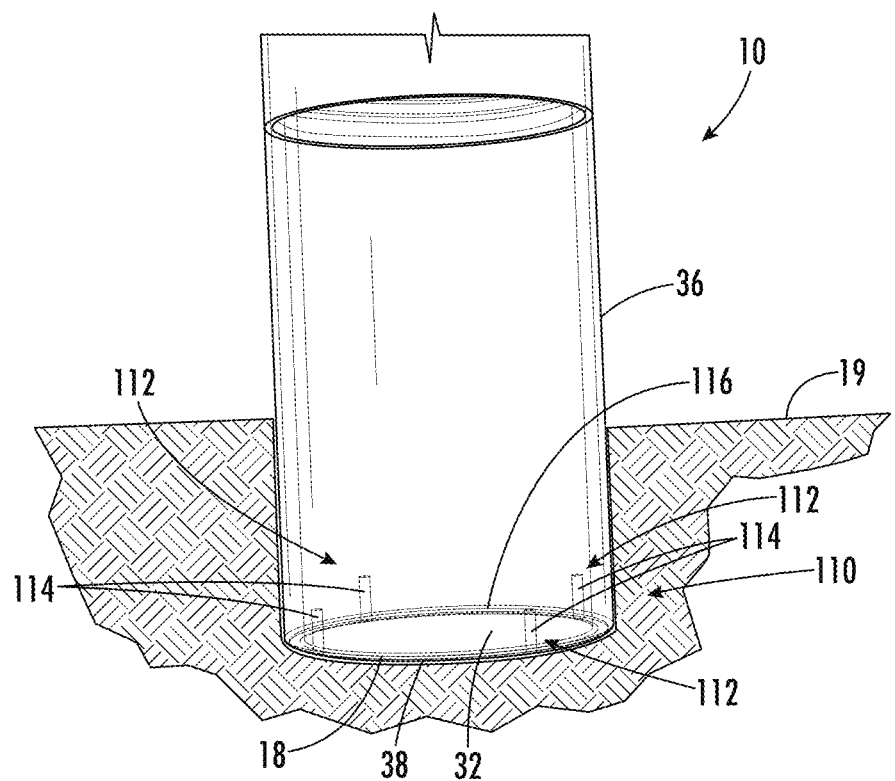
FIG. 19 is a perspective view of a detachable segment with a positioning system attached thereto.

The modular access medical system 10, as shown in FIG. 19, may include a positioning system 110 configured to assist in positioning the distal end 38 of the at least one detachable segment 36 within a patient 19. The positioning system 110 may be, but is not limited to being, one or more indicators 112 configured to be viewable by an imaging system such as, but not limited to, fluoroscopy. In at least one embodiment, the positioning system 110 may be, but is not limited to being, one or more metal indicators 112 configured to enable a surgeon to use an imaging system to identify the location of the metal indicator 112 and thus, the position of the distal end 38 of the detachable segment 36 within a patient 19. In at least one embodiment, the metal indicator 112 may be positioned within the detachable segment 36. The metal indicator 112 may be, but is not required to be, positioned at or near the distal end 38 of the detachable segment 36. The positioning system 110 may be, but is not limited to being, one or more pins 114 positioned at the distal end 38 of the detachable segment 36. The pin 114 may be, but is not limited to being, a metal dowel pin configured to be seen via an imaging system, such as, but not limited to, fluoroscopy, to determine the location of the metal dowel pin 114 relative to a patient's anatomy. The positioning system 110 may be, but is not limited to being, one or more rings 116, which may be positioned at or near the distal end 38 of the detachable segment 36. The positioning system 110 may be, but is not limited to being, the distal detachable segment 36 formed from a metal that is visible via an imaging system and resistant to high temperatures created via ablation procedures.

The modular access medical system 10, as shown in FIG. 18, may include a camera positioning system 120 configured to adjustably position a camera 122 within the one or more detachable segments 36 at a desired depth and retain the camera 122 in the position until desired to move into another position. In at least one embodiment, the camera positioning system 120 may be formed from one or more instrument receiving slits 52 configured to receive an instrument 16 extending therethrough while being configured to be biased to a resting position in which the slit 52 remains closed. The camera positioning system 120 may create an interference fit between a camera shaft 124 and the dam 50 in the slit. In other embodiments, the camera positioning system 120 may include set screws, ball detents, a track system and the like to retain a shaft 124 supporting the camera 122, and thus, the camera 122, in a desire position.

Figure 13:
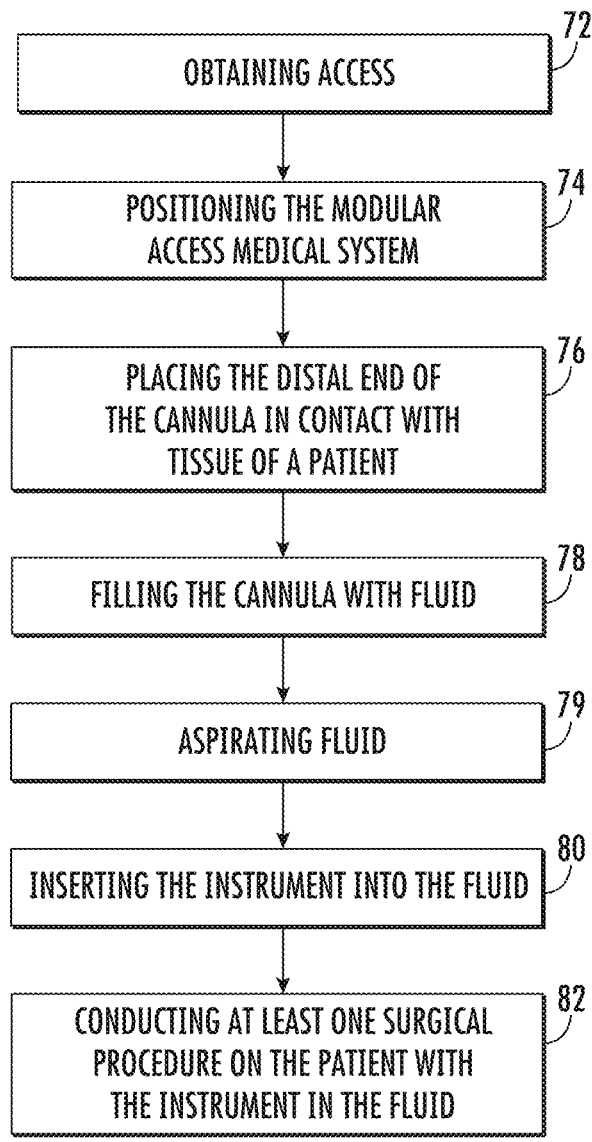
FIG. 13 is a flow diagram of the method of using the modular access medical system to perform a medical procedure.

In at least one embodiment, the modular access medical system 10 may be used in a method 70, as shown in FIG. 13, of conducting a surgical procedure on a patient to increase visibility of a surgeon by conducting surgery with an instrument 16 in fluid 12, thereby eliminating vision obstructing smoke, vapor and the like often caused by use of the instrument 16 on a patient 19. The method 70 may include obtaining access at step 72 to a target surgical site 18 within a patient 19. A surgeon or other qualified person may obtain access to a target surgical site 18 via any appropriate method of exposing or providing an opening to the target site 18 to the ambient environment.

The method 70 also may include positioning at step 74 at least a portion of the modular access medical system 10 within the patient 19. Positioning at step 74 may include positioning one or more of the embodiments of the modular access medical system 10 previously set forth. In particular, the positioning at step 74 may include positioning the modular access medical system 10 formed from a housing 26 having a working channel 28 with a proximal opening 30 and a distal opening 32; a cannula 22 extending distally from the housing 26 and forming a channel 34 extending therethrough for receiving one or more instruments 16, whereby the channel 34 in the cannula 22 is aligned with the working channel 28 of the housing 26; and wherein a distal end 38 of the cannula 22 is configured to be placed into contact with tissue such that fluid can be administered within the cannula 22 and retained therein to facilitate a surgical procedure to be conducted via the instrument 16 extending through fluid contained within the cannula 22. The step 74 may include positioning one or more of the embodiments of the modular access medical system 10 including a dam 50 to retain the fluids within the cannula 22. The dam 50 may be held removably in position in the housing 26 via the dam retention system 90.

The method 70 may include placing at the step 76 the distal end 38 of the cannula 22 in contact with tissue of a patient 19 to seal the distal end 38. The step 76 the distal end 38 of the cannula 22 in contact with tissue of a patient 19 may include using positioning system 110 to assist in positioning the distal end 38 of the at least one detachable segment 36 within a patient 19. In particular, an imaging system may be used to determine a location of the distal end 38 of the cannula 22 to assist a surgeon in moving the distal end 38 of the cannula 22 into a desired position within a patient 19.

The method 70 may include filling at step 78 the cannula 22 with fluid 12. The fluid used to fill the detachable segment 36 may be, but is not limited to being, saline fluid and other appropriate fluids. Fluid may be filled in the cannula 22 via the inflow port 46. The inflow port 46 may be directed distally, via the enhanced fluid exchange section 47, so that fluid may not only fill the cannula 22 but may be continuously or intermittingly replace the fluid within the cannula 22 during a surgical procedure to maintain good visibility throughout the duration of the surgical procedure. The method 70 may include filling at step 78 the cannula 22 with fluid 12 such that an upper surface 62 of the fluid 12 is aligned with a lower edge 64 of an aspiration port 40 in the housing 26.

The method 70 may also include aspirating fluid at step 79 to remove excess fluid so that fluid does not flow out of the proximal opening 30 in the housing 26. Aspirating fluid at step 79 may be continuous to maintain a desired fluid level. The cannula 22 may also be topped off with fluid throughout a procedure to account for fluid leaking from the distal end 38 of the cannula 22 formed by the detachable segment 36.

The method 70 may include inserting at step 80 the instrument into the fluid 12. The method 70 may include conducting at step 82 one or more surgical procedures on the patient 19 with the instrument 16 in the fluid 12. The method 70 may include using a cannula 22 extending distally from the housing 26 whereby the cannula 22 is formed from one or more detachable segments 36. The method 70 may include using one or more detachable segments 36 formed from a plurality of detachable segments 36 coupled together, wherein the plurality of detachable segments 36 are different lengths.

The step of inserting 80 the instrument 16 into the fluid 12 may include inserting at least a portion of the instrument 16 through dam 50 positioned in the housing 26 to retain the fluids 12 in the working channel 28 of the housing 26. The step of inserting 80 the instrument 16 into the fluid 12 may include retaining the instrument in place via the instrument securement system 54, as previously set forth. The step of inserting 80 the instrument 16 into the fluid 12 may include retaining a camera or other instrument 16 in position via the camera positioning system 120.

The foregoing is provided for purposes of illustrating, explaining, and describing embodiments of this invention. Modifications and adaptations to these embodiments will be apparent to those skilled in the art and may be made without departing from the scope or spirit of this invention.

We claim:
1. A modular access medical system, comprising:
a housing having a working channel, a proximal opening providing access to the working channel and a distal opening providing access to the working channel;

a cannula extending distally from the housing and defining a channel extending therethrough for receiving at least one instrument, whereby the channel in the cannula is aligned with the working channel of the housing;

wherein the cannula is defined by at least one detachable segment;

wherein a distal end of the at least one detachable segment is configured to be placed into contact with tissue such that fluid can be administered within the cannula and retained therein to facilitate a surgical procedure to be conducted via the at least one instrument extending through fluid contained within the cannula;

at least one dam positioned in the housing to retain the fluids in the working channel of the housing to seal the working channel of the housing to prevent fluids from passing from the channel in the detachable segments out of the proximal opening of the working channel of the housing;

at least one dam retention system configured to removably attach the dam to the housing; and wherein the at least one dam retention system comprises at least one arm extending radially outward from the at least one dam and at least one slot configured to releasably receive the at least one arm.

2. The modular access medical system of claim 1, wherein the at least one detachable segment defining the cannula comprises a plurality of detachable segments coupled together and extending distally from the housing, wherein at least one of the plurality of detachable segments has a different length than other detachable segments.

3. The modular access medical system of claim 1, further comprising an aspiration port coupled to the housing, wherein an aspiration channel extends from a proximal opening in the aspiration port, through the housing, and terminates at the working channel of the housing, thereby enabling the modular access medical system to maintain the cannula defined by the at least one detachable segment full of fluid during use.

4. The modular access medical system of claim 1, further comprising an inflow port comprising an enhanced fluid exchange section which includes a distally directed vector such that an outlet of enhanced fluid exchange section is closer to the distal end of the at least one detachable segment than an inlet of the enhanced fluid exchange section.

5. The modular access medical system of claim 1, wherein the at least one dam positioned in the housing to retain the fluids in the working channel of the housing comprises at least one instrument receiving slit configured to receive an instrument extending therethrough while being configured to be biased to a resting position in which the slit remains closed.

6. The modular access medical system of claim 1, further comprising a camera positioning system configured to adjustably position a camera within the at least one detachable segment at a desired depth and retain the camera in position until desired to move into another position.

7. The modular access medical system of claim 1, further comprising an instrument securement system positioned adjacent the housing for retaining an instrument in position within the channel in the at least one detachable segment.

8. The modular access medical system of claim 7, wherein the instrument securement system comprises at least one receiver positioned in an outer surface of the housing.

9. The modular access medical system of claim 1, further comprising a positioning system configured to assist in positioning the distal end of the at least one detachable segment within a patient with the use of an indicator visible with an imaging system.

10. A method of using an instrument within a patient via a modular access medical system, comprising:

obtaining access to a target surgical site within a patient;

positioning at least a portion of the modular access medical system within the patient, wherein the modular access medical system, comprises:

a housing having a working channel, a proximal opening providing access to the working channel and a distal opening providing access to the working channel;

a cannula extending distally from the housing and defining a channel extending therethrough for receiving the instrument, whereby the channel in the cannula is aligned with the working channel of the housing;

wherein a distal end of the cannula is configured to be placed into contact with tissue such that fluid can be administered within the cannula and retained therein to facilitate a surgical procedure to be conducted via the instrument extending through fluid contained within the cannula;

at least one dam positioned in the housing to retain the fluids in the working channel of the housing to seal the working channel of the housing to prevent fluids from passing from the channel in the detachable segments out of the proximal opening of the working channel of the housing;

at least one dam retention system configured to removably attach the dam to the housing; and wherein the at least one dam retention system comprises at least one arm extending radially outward from the at least one dam and at least one slot configured to releasably receive the at least one arm;

placing the distal end of the cannula in contact with tissue of a patient to seal the distal end;

filling the cannula with fluid;

inserting the instrument into the fluid; and using the instrument on the patient in the fluid contained in the cannula.

11. The method of claim 10, wherein the cannula extending distally from the housing is defined by at least one detachable segment.

12. The method of claim 11, wherein the at least one detachable segment is defined by a plurality of detachable segments coupled together, wherein the plurality of detachable segments are different lengths.

13. The method of claim 11, wherein filling the cannula with fluid comprises filling the cannula with fluid such that an upper surface of the fluid is aligned with a lower edge of an aspiration port in the housing.

14. The method of claim 11, wherein inserting the instrument into the fluid comprises inserting at least a portion of the instrument through at least one dam positioned in the housing to retain the fluids in the working channel of the housing.

15. The method of claim 11, wherein inserting the instrument into the fluid comprises using a positioning system on the at least one detachable segment to assist in positioning the distal end of the at least one detachable segment with a patient.

16. The method of claim 11, wherein filling the cannula with fluid comprises filling the cannula with fluid via an enhanced fluid exchange section of an inflow port.

17. The method of claim 11, wherein inserting the instrument into the fluid comprises retaining the instrument in place via an instrument securement system.

18. The method of claim 11, wherein inserting the instrument into the fluid comprises retaining a camera in position via a camera positioning system.

19. A method of using an instrument within a patient via a modular access medical system, comprising:

obtaining access to a target surgical site within a patient;

positioning at least a portion of the modular access medical system within the patient, wherein the modular access medical system, comprises:

a housing having a working channel, a proximal opening providing access to the working channel and a distal opening providing access to the working channel;

a cannula extending distally from the housing and defining a channel extending therethrough for receiving the instrument, whereby the channel in the cannula is aligned with the working channel of the housing;

wherein a distal end of the cannula is configured to be placed into contact with tissue such that fluid can be administered within the cannula and retained therein to facilitate a surgical procedure to be conducted via the instrument extending through fluid contained within the cannula;

at least one dam positioned in the housing to retain the fluids in the working channel of the housing to seal the working channel of the housing to prevent fluids from passing from the channel in the detachable segments out of the proximal opening of the working channel of the housing;

at least one dam retention system configured to removably attach the dam to the housing; and wherein the at least one dam retention system comprises at least one arm extending radially outward from the at least one dam and at least one slot configured to releasably receive the at least one arm;

placing the distal end of the cannula in contact with tissue of a patient to seal the distal end;

filling the cannula with fluid such that an upper surface of the fluid is level with a lower edge of an aspiration port;

inserting the instrument into the fluid; and using the instrument on the patient in the fluid contained in the cannula.

20. The method of claim 19, wherein filling the cannula with fluid such that an upper surface of the fluid is level with a lower edge of an aspiration port and wherein the aspiration port is positioned in the housing.

21. The method of claim 19, wherein the cannula extending distally from the housing is defined by a plurality of detachable segments coupled together, wherein the plurality of detachable segments are different lengths.

* * * * *